(12) United States Patent
Goertler (10) Patent No.: US 11,031,125 B2
(45) Date of Patent: Jun. 8, 2021

(54) IDENTIFICATION OF STRUCTURAL PARTS IN ERROR HANDLING OF MEDICAL DEVICES

(71) Applicant: Siemens Healthcare GmbH, Erlangen (DE)

(72) Inventor: Georg Goertler, Baiersdorf (DE)

(73) Assignee: Siemens Healthcare GmbH, Erlangen (DE)

( * ) Notice: Subject to any disclaimer, the term of this patent is extended or adjusted under 35 U.S.C. 154(b) by 310 days.

(21) Appl. No.: 16/168,921

(22) Filed: Oct. 24, 2018

(65) Prior Publication Data

US 2019/0122761 A1 Apr. 25, 2019

(30) Foreign Application Priority Data

Oct. 24, 2017 (EP) ..................................... 17197958

(51) Int. Cl.
*G16H 40/40* (2018.01)
*G05B 23/02* (2006.01)
*G16H 40/60* (2018.01)

(52) U.S. Cl.
CPC ......... *G16H 40/40* (2018.01); *G05B 23/0218* (2013.01); *G16H 40/60* (2018.01)

(58) Field of Classification Search
None
See application file for complete search history.

(56) References Cited

U.S. PATENT DOCUMENTS

| 9,052,711 B2* | 6/2015 | Schneider .......... G05B 23/0262 |
| 2004/0193958 A1 | 9/2004 | Shah et al. |
| 2009/0125757 A1 | 5/2009 | Knorl et al. |
| 2011/0302461 A1 | 12/2011 | Goertler et al. |
| 2018/0286510 A1* | 10/2018 | Kwan ................ G06Q 30/0633 |

* cited by examiner

*Primary Examiner* — Roy Y Yi
(74) *Attorney, Agent, or Firm* — Schiff Hardin LLP (57) ABSTRACT

In a method, a database system, a computer, and a medical system for the identification of faulty structural parts to be exchanged of a medical device, an identification algorithm is executed to calculate and emit an exchange data record that identifies a structural part to be exchanged, dependent on for a read-in error message from the medical device. The identification algorithm accesses a database system with a simulation model in which automatically generated error patterns (are stored in order to perform an analysis on these stored error patterns, so as to calculate the exchange data record. An error pattern is an association between the error message, an exchange data record, and an evaluation data record.

25 Claims, 3 Drawing Sheets

FIG 6

IDENTIFICATION OF STRUCTURAL PARTS IN ERROR HANDLING OF MEDICAL DEVICES

BACKGROUND OF THE INVENTION

Field of the Invention

The present invention relates to a method and a database system, a calculation processor and a system and a non-transitory, computer-readable data storage medium for the identification of faulty structural parts to be exchanged in a medical device that can be operated in a group of medical devices.

Description of the Prior Art

In clinical operations, lengthy outages of medical devices are frequently unacceptable and therefore time-critical. The time phase in which a replacement part is sought and the faulty structural part replaced by a replacement part must be as short as possible in order to minimize device outage time.

It is known to use computer-assisted methods to improve servicing of medical devices. These methods are sometimes based on the set of available data in order to be able to derive information therefrom. However, if only a small amount of data is available, for example with a new product, immediately after product release, problems may arise with these methods because as yet there is no, or too little, operating data available.

SUMMARY OF THE INVENTION

An object of the present invention is to expand such a database in order, in an error scenario, to be able to use an automatic method at an early stage of the product cycle so as to ascertain which structural part in a complex medical device is to be exchanged. Overall, the operating times of the devices and error handling in an error scenario are to be improved. In particular, the search for an adequate replacement part is to be accelerated.

According to a first aspect, the object is achieved by a method for the identification of structural parts of a medical device that are to be exchanged (because they are faulty). The medical device has multiple, possibly different, structural parts. The medical device can be an MR device. The method has the following method steps. An error message is read into a computer from the medical devices. An identification algorithm is executed in the computer for calculating and emitting an exchange data record for the read-in error message, wherein the exchange data record identifies a structural part to be exchanged. For this purpose, in the execution of the identification algorithm with the read-in error message a database system is accessed by the computer in which error patterns with exchange data records are stored that have been calculated from a simulation model. The identification algorithm then calculate, as the algorithm result, the stored exchange data record associated with the read-in error message.

The invention thus expands the database for storing error patterns continuously by using machine-based methods and algorithms in order to be able to provide the result for a detected error scenario with optimum quality at an early stage of the product life cycle of the device, and in particular immediately after the release of the device. The result should identify a structural part for exchange based on reference data. The reference data includes test data from test operation and simulation data from a simulation model. The simulation model is expanded continuously during test operation and also during real device operation in the field.

In an embodiment of the method, the execution of the identification algorithm is triggered by the reading-in of the error message. Hence, the method can be operated as a proactive method. This has the advantage that the result can be provided automatically and more quickly since it is not necessary first to wait for a manual input or request.

The method can even be carried out completely without any operating data and immediately after the first commissioning or product release of the medical device. This is enabled by a simulation model being generated and used, which, in addition to the test data, also provides simulation data that are used as input variables to generate error patterns. This has the advantage that the method can be used as early as the first commissioning, even if no operating data are yet available. This is enabled because the database is expanded with reference data, i.e. test data, collected in a development phase and additionally with simulated data.

In another embodiment of the method, the identification algorithm is embodied as a self-learning system. To this end, the calculated exchange data record for the respective error message (iteratively and continuously)—and optionally: an associated evaluation data record—is entered into the database system. This enables the quality of the result to be improved.

The object is further achieved with a database system for use in the above-described method. The database system is used to store error patterns, which are generated automatically by operation of an error pattern generation processor, wherein the error pattern generation processor is embodied to execute a machine-learning method based on a simulation model that enables the continuous learning and storage of error patterns by the correlation of input variables, wherein in each case an error pattern designates an association between an error type (or a combination of error types) of an error message and an exchange data record indicating a structural part to be exchanged.

In an embodiment of the database system, to generate the error patterns, the error pattern generation processor reads in test data, aggregated as input variables, from a test operation with error scenarios of the medical device and associated exchange data records in order to generate error patterns therefrom. The test data are therefore acquired in a development phase of the device and in particular still before the release of the device. Preferably, in each case an exchange data record (which uniquely references the structural part replaced on a test basis) and an evaluation data record are associated with the respective error scenarios in the test operation (test data) and stored as a pattern. The evaluation data record enables the identification of the quality assessment of the error correction measure (the exchange).

A simulation model is generated in parallel with the test operation of the device. The simulation model enables the expansion of the database with simulation data calculated from the data aggregated so far (test operation and later also in the real device operation with operating data). The aggregated data includes a data field for identifying the respective error, associated exchange data records and evaluation data records. This aggregated data can also originate from other devices of the same type (for example the same modality or a device with predefinable matching technical criteria). According to an embodiment of the invention, it is also possible to use test data from other devices of the same type as the device from which the error message was received. This expands the database and makes it possible to obtain the test or training data earlier or more quickly in order to use them for the calculations.

In a further embodiment of the database system, the simulation model is not only continuously updated during the test operation in the development phase, but it can instead also be expanded later in the product life cycle, namely during real operation with operating data. This enables the quality of the error correction measure by structural part exchange to be continuously updated. This is achieved by the database being embodied to generate the error patterns as a self-learning system and is constantly expanded. This further has the advantage that the automatic structural part identification method can be carried out in the product cycle before and even immediately after product release without the existence of operating data. In this embodiment of the invention, the device is tested in a development phase. To this end, predefinable test cases are generated, partially also in order to intentionally generate errors that are then detected. The structural parts exchanged in order to rectify the detected error (on a test basis) are then acquired as an exchange data record and stored in the database system. The quality of the error rectification by the structural part exchange (in other words: replacement of the faulty structural part by a new or non-faulty structural part) is evaluated by the evaluation data record and also stored. The aforementioned collected data (error message, exchange data record, evaluation data record) is then available by association (namely as error patterns) in the database of the database system for future error scenarios. For a specific error message, the error patterns held resident can be used as the basis for carrying out an analysis in the stored data in order to calculate the exchange data record suitable for the error scenario.

In a further embodiment of the database system, said system is embodied as a central entity for a number of medical devices. This enables the scope of the error patterns generated to be expanded and the informative value of the result to be improved.

In another embodiment of the database system, the error pattern generation processor interacts with a rule base in which rules for generating the error patterns are stored. The rules can be predefined. The rules are preferably dynamically adjustable. Hence, advantageously, the method can be adapted very flexibly to the particular application and operation of the device.

One rule can be, for example, a processing sequence first A then B, or A and B in any sequence.

In another case, the rule can cause only the most probable error patterns to be used or system-specific or country-specific specifications of rules are possible.

In a further embodiment of the database system, to generate error patterns, the error pattern generation processor takes account of evaluation data or evaluation data records representing a measure of the quality of the respective error correction that has already been performed and which has been acquired and stored during historical structural part replacements to form an error message.

In a further embodiment for generating the error patterns, the database system and/or the error pattern generation processor can use a method for machine learning, such as to carry out Markov processes (Markov chains).

In another embodiment, the processor can enable the use of data mining methods and/or the use statistical and stochastic methods for data processing.

The above object mentioned also is achieved by a calculation processor, which can be embodied as a central server, which enables the provision of a structural part identification service that operates according to any of the above-described method embodiments and, to this end, interacts with the database system. The calculation processor has an input interface that reads in an error message from a medical device, an identification processor configured to use the identification algorithm to calculate the exchange data record, and an output interface from the calculated exchange data record is emitted in electronic form, such as a data file, as an output.

The input and output interfaces are to be understood as logical interfaces. They enable and regulate the exchange of commands and data between different processes and components of the database system or the calculation processor.

The above object also is achieved by a medical system with units connected via a network, having multiple medical devices, in particular MR devices, each having multiple structural parts, a calculation processor as described above, and a database system as described above.

The present invention also encompasses a non-transitory, computer-readable data storage medium encoded with programming instructions (program code) that, when the storage medium is loaded into a computer, cause the computer to implement any or all embodiments of the method according to the invention, as described above.

The following defines the terms used herein.

The medical device is a complex medical apparatus consisting of different electronic, mechanical and/or physical structural parts. The medical device can have a purely medical purpose (for example image acquisition) or a technical purpose (for example data compression, image post-processing, device control) in the medical environment. The device, for example, can enable image acquisition and/or technical processing in the field of medicine. The term "device" in the following means the medical device. It can, for example, be an MRI device, a CT device or the like. The device can be operated in a group of devices of the same or different types in a device group.

The structural parts can be integrated in the device or be in data exchange therewith. The structural parts can enable different functions of the device. A structural part of an MR device can, for example, be a superconducting magnet, a cooling unit, a gradient coil, a surface coil, a computing unit or a communication connection for data exchange. The structural parts are (in particular in an error scenario) arranged in an exchangeable manner in the device and can be replaced by other (non-faulty) structural parts of the same type.

The simulation model is generated on a computer basis and enables the modeling of error scenarios of the device in order to find suitable error correction measures by exchanging one or more structural parts of the device. The simulation model can be a descriptive simulation model for error rectification. The simulation model is preferably embodied as a continuous model. It operates in an event-driven manner in dependence on the occurrence of a new error scenario (in test operation or in the real operation of the device). The use of the simulation model enables the quality of the result to be optimized with a proposal for a structural part exchange in an error scenario.

A simulation model can, for example, represent a Markov chain or be trained by means of a neural network which has learned transition probabilities of messages. This enables numerous log files to be simulated which also contain error patterns with a certain probability. These are then independent of the individual system and contain a plurality of log file variants, which can also be learned. The optimization of the simulation model can be improved by training and comparison with the test system or the real system.

An error message is an electronic data record, which can be exchanged as a message via a network with other entities. The error message enables the identification of an error or an error condition (combination of errors) which has been detected on a device. The error message is preferably device-specific. However, the error message is not specific to a structural part so that, as a rule, it is not possible to draw conclusions regarding a faulty structural part that is to be exchanged from an analysis of the error message. The error message can have a specific structure, which can, for example, correspond to a standard (for example DICOM, Digital Imaging and Communication in Medicine). The error message can have different technical causes. The error message is usually device-specific and can describe a state of a device. As a rule, it is not possible to derive the cause of an error directly and readily from the error message. This means that, as a rule, extensive technical knowledge is required in order to draw conclusions regarding a structural part to be exchanged from an error message.

The identification algorithm enables the identification of a faulty structural part to be replaced in order to rectify the fault condition or fault in the device. To this end, the read-in error message is analyzed as input data and compared with further data records and, for example, compared with reference data (in a database system). The identification algorithm is able to take account of still further data as input data. The result (output data) supplied by the identification algorithm is an exchange data record. The identification algorithm is implemented in software and can be executed on a computer with a commercially available operating system. The identification algorithm is executed by one identification processor. The identification algorithm can also be executed distributed among different processors or can be provided centrally by a server as a service. The identification algorithm can be executed on all or selected devices as a client application and/or on a central server as a service. The identification algorithm performs an analysis on the stored error patterns with regard to the read-in error message.

The exchange data record is an electronic data record which is structured according to predefinable rules and calculated by the identification unit and provided as a result. The exchange data record uniquely identifies the structural part on the device which is faulty or has to be exchanged in order to correct the error. Hence, the exchange data record uniquely references a structural part of a device with regard to an error message. In the simplest case, the exchange data record can be a unique structural part number or material number.

In a preferred embodiment of the invention, the exchange data record can include further data fields with metadata, in particular a validation data field for the evaluation of the informative value of the calculated exchange data record. The validation data field can in particular comprise data relating to correctness and test coverage. This has in particular been found to be advantageous for the quality of the error rectification in the case of the earlier application of the simulation model and if statistical methods have been used for the testing.

The database system has a database, in particular a relational database, and a database management system for technical data processing. This can be a data memory and a processor as a calculation processor. The database system has an error pattern generation processor.

The error pattern generation processor enables the automatic and computer-implemented generation of error patterns that are stored in the database system. The error pattern generation processor can be arranged directly in the database system or it can be connected as a separate entity via interfaces.

An error pattern is an electronic data structure which is calculated automatically. An error pattern is calculated by a correlation of different data records that are read from an error log file and/or other files provided by the device and which relate to a specific type of error or a group of error types. The correlation and calculation of the error pattern is performed according to specific predefinable rules. This is based on a set of rules which (can be stored in a rule database and) enables the grouping and classification of the different error messages for the different devices into error types (for example messages on the device status, such as "power supply absent/interrupted" or "missing data record") or into groups of error types (for example error types relating to a specific structural part or a component of a structural part). At least one exchange data record is assigned to the error type or the group of error types of an error pattern. Insofar, an error pattern can also be called an exchange pattern.

The error pattern can be calculated as a metric pattern in a first embodiment and as a structural part pattern in a second embodiment of the invention.

In the first embodiment, to generate the error patterns, the data from the log files generated during the operation (for example also during the measurements) of the devices is preprocessed in order to correlate this preprocessed data with device messages (representing a device status, such as the interruption of a scan or image acquisition). Then, correlation information can be extracted from the correlated data records so that it is then possible to apply data mining methods to the complete event recording files of the devices (eventlog) with this correlation information.

In the second embodiment of the invention, to generate the error patterns, the device messages are correlated directly with device status data in order to interrupt scans. This correlation information is then used by applying data mining methods and with the complete event log files of the devices (eventlogs) in order to generate the error patterns. The device messages represent an operating status of the device and can, for example, comprise fields for the following information: start of an outage or stoppage phase of the device (downtime start), end of the outage or stoppage phase (downtime end), the identification number of the respective device and the structural parts replaced in response to the error.

The error patterns generated can be stored in a tabular-like data structure and/or can be shown on a graphical user interface in the form of a two-dimensional depiction. The error patterns can also comprise an evaluation data record which indicates how well it was possible to correct the error by the structural part exchange. The error patterns also can be generated such that the respective data records are grouped based on the evaluation data and hence the sequence of the error patterns correlates with a quality of the error correction.

The error patterns of historical, i.e. already performed, structural part replacements for past error messages are all stored in the database system. In addition, the associated exchange data (i.e. the replaced structural part in each case) and optionally an evaluation data record representing the quality of the error correction, are stored. This historical data (for already performed structural part replacements and evaluations in this respect) is analyzed by the identification algorithm for the calculation of the respective current exchange data record (in response to the current error message).

The error pattern is generated by means of the error pattern generation unit by the correlation of input variables. An error pattern is preferably specific to a specific device type (for example an MR device of the type xyz). It is hence possible to aggregate error patterns for different types of device. The method to generate the error patterns is implemented on the error pattern generation processor of the database system or on an external computing unit located outside the database system.

The input variables are preferably also stored in the database. The input variables comprise device messages on faulty operating states of one of the devices, exchange data records and evaluation data records.

The system and in particular the identification algorithm are embodied as a self-learning system. This means that the database is continuously and constantly expanded and hence the quality of the information is improved with each new error message and application.

The calculation processor can be implemented in software and/or in hardware. The calculation processor can be a group of devices, a medical device or a central server in order to be able to provide the identification service as a central service for a plurality of devices. The calculation processor is preferably embodied with an output interface (browser, GUI, data interface etc.) to output the exchange data record. To calculate the exchange data record, the method can advantageously be carried out centrally for a number of sometimes also different medical devices (also in parallel or alternatively locally on a device with a network connection to the centrally held database system).

The identification processor is a hardware-based solution and enables the execution of the identification algorithm. The error pattern generation processor also corresponds to a hardware-based solution and enables the performance of a method for the generation of error patterns that is implemented in software. Features, advantages or alternative embodiments can also be transferred to the other claimed subject matter and vice versa. In other words, the material features and claims (which are, for example, directed at a system, a calculation processor or a computer program product) can be developed with the features that are described or claimed in connection with the respective method. Herein, the corresponding functional features of the method are embodied by corresponding material modules, in particular by hardware modules or microprocessor modules, of the system or the product and vice versa.

DESCRIPTION OF THE PREFERRED EMBODIMENTS

Figure 1:
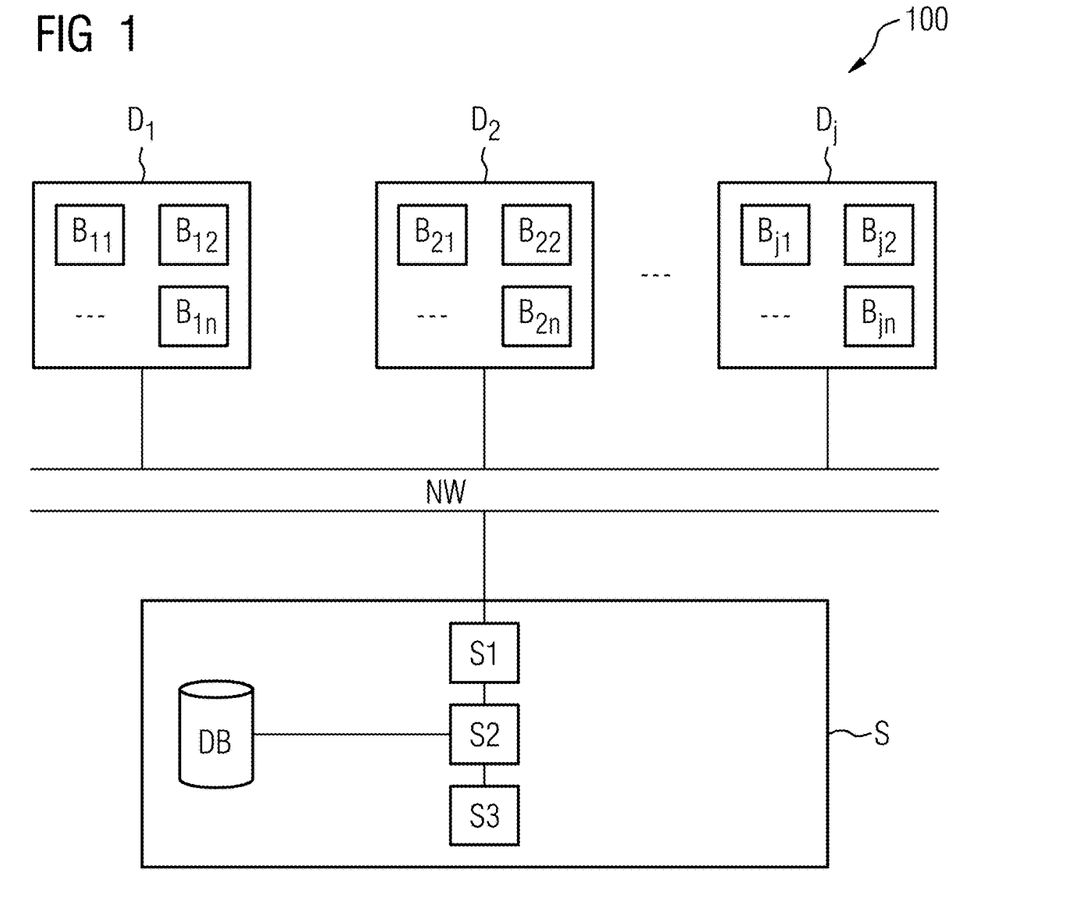
FIG. 1 is a block diagram of a system according to a preferred embodiment of the invention.

FIG. 1 is a schematic overview of a system 100. The system 100 has a number of separate devices, which are denoted in the following by the reference characters $D_1$, $D_2, \ldots D_j$. The devices are technical, in particular medical devices, such as image acquisition systems, such as inter alia magnetic resonance imaging devices, computed tomography scanners, ultrasound devices and the like. As is known to those skilled in the art, these devices have a high degree of complexity and are each composed of multiple components and structural parts B. As depicted in FIG. 1, each medical device $D_1$, $D_2$, $D_j$ is characterized by a number of different components and structural parts, which are identified in FIG. 1 with the reference characters $B_{11}$, $B_{12}$, $B_{1n}$ for a first medical device $D_1$ and with $B_{j1}$, $B_{j2}$, ... $B_{jn}$ for an j-th medical device $D_j$. All the medical devices are connected to one another via a network NW and are able to interact or exchange data. Furthermore, the medical devices D are connected to a calculation processor S, which can be embodied as a central server and enables the provision of a structural part identification service. To this end, the calculation processor S interacts with a database system DB, which, in the exemplary embodiment depicted in FIG. 1, is arranged inside the calculation processor S. In an alternative embodiment, however, the database system DB can be connected as an external entity via corresponding interfaces to the calculation processor S (this will be the preferred embodiment). To provide the structural part identification service, the calculation processor S has a number of electronic components: an input interface S1, which is provided to read in error messages fm from one of the medical devices D. In addition, the calculation processor S includes an identification processor S2, which is configured to apply an identification algorithm 22 to calculate an exchange data record ad. The calculation processor S further has an output interface S3, which is provided to emit the exchange data record ad calculated as the result. This can be, for example, a graphical user interface (GUI) or interfaces to attached clients and/or servers.

Figure 2:
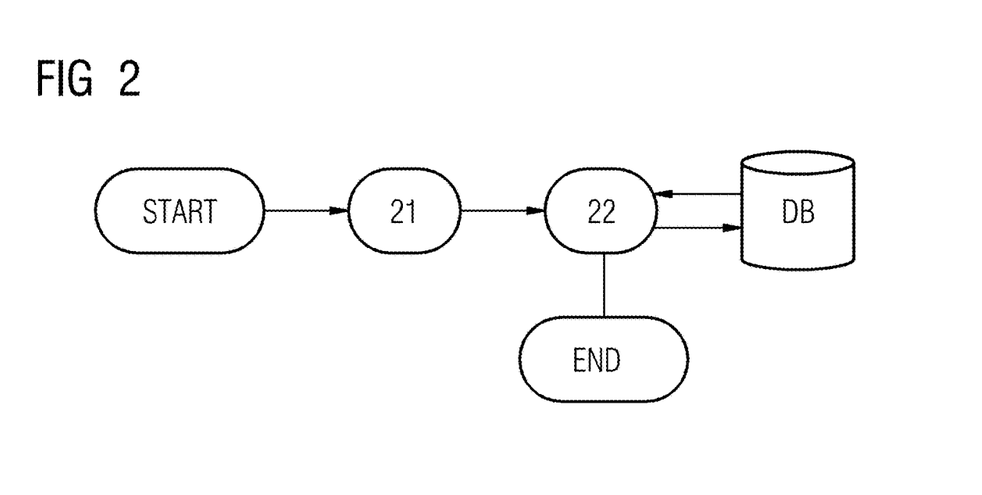
FIG. 2 is a flowchart diagram of the method for the identification of structural parts to be replaced according to a preferred embodiment of the invention.

The calculation processor S enables the performance of an identification method, which is described in more detail in the following with reference to FIG. 2.

After the start of the method for the identification of structural parts B of a medical device to be exchanged, in step 21, in each case, an error message fm from one of the devices D is read-in. Herein, the system is not restricted with respect to how many error messages fm are received per unit of time. The inventive method and the other aspects of the invention also can process error messages fm received in parallel. The reading-in in step 21 preferably takes place in an operating phase of the device, i.e. as a rule during the clinical use of an MR device D, for example.

Step 22 entails the execution of the identification algorithm for calculating and outputting an exchange data record ad, which identifies a structural part B to be exchanged specifically in response to the acquired error message fm. Hence, the exchange data record ad is specific to the structural part and specific to the error message. The identification algorithm 22 can be executed on any computer or computing unit or a group of computing units or a processor of a computer. For the calculation, the identification algorithm 22 accesses the database system DB in which error patterns fmu with exchange data records ad and associated evaluation data records bd are stored. Access to the database system DB takes place in a dedicated manner for the read-in error message fm in order to calculate specifically for this read-in error message fm from the error patterns fmu stored in the database system DB an exchange data record ad, which is associated with the read-in error message fm and has the highest possible quality, i.e. has an optimum exchange result with respect to the solution to the problem. This enables it to be ensured that, as far as possible, the result of the identification algorithm 22 only indicates the structural parts B which are responsible for the error identified in the error message fm and the exchange or replacement of which results in the correction of the error. The result of the identification algorithm 22 can be output in a following method step and in particular on an output interface or provided for retrieval or downloading.

As explained above, error patterns fmu that serve to calculate exchange data records ad are stored in the database system DB. Therefore, an important aspect of the present invention consists in the generation of the error patterns fmu in the database system DB. This is explained in more detail in the following.

An error pattern generation processor FME is provided for the generation of the error patterns fmu. This can be embodied as a computer-based unit comprising hardware and software. Hence, the error pattern generation unit FME can also be embodied as a processor which enables the execution of an algorithm for error-pattern generation. The algorithm for error-pattern generation is based on machine-learning methods.

The error-pattern generation accesses the simulation model. As a rule, the simulation model is characterized by the generation of simulation data based on acquired data (i.e. data from test operation or from device operation in the field). The simulation model enables the application of learned data, patterns and regularities in order to generate new data (simulated data). The machine-learning methods used according to the invention are based on input variables, which have been extracted from historically acquired error messages from different medical devices D. The input variables comprise, on the one hand, the respective error message from the respective medical device D, the structural part exchanged in respect of this error message. As an important further feature, the input variables additionally comprise evaluation data bd (or an evaluation data record), which serves as a measure of the quality of the already performed (earlier) historical error correction by the exchange of the respective structural part B. In other words, the evaluation data bd, characterizes the effectiveness of the correction of the respective error (represented in the error message fm) by the exchange of the respective structural part B. Hence, the quality or the effectiveness of the historical error correction measure is included in the generation of error patterns of the error pattern generation unit FME. This ensures a continuous and iterative learning process.

The error pattern generation processor FME is embodied to generate the error patterns fmu by correlation of the (continuously re-entered) input variables. An error pattern fmu, which has been generated accordingly, comprises an assignment between an error type (for example complete or partial failure of a structural part B or partially disrupted communication connection etc.) or a combination of error types and an exchange data record ad. Hence, the exchange data record ad relates to historical exchanges which have been performed due to an error message fm. The exchange data record ad characterizes the structural part exchanged at the time. As already mentioned above, the created error patterns fmu also represent a classification of the quality of the error correction at the time, which is represented in the evaluation data bd. The error pattern generation processor FME creates error patterns from these input variables. These are stored continuously in the database system DB and enriched in each case with new learning processes. Hence, the error patterns fmu created and stored in this way are stored in the database system DB and are used by the identification method in order to calculate the exchange data record ad.

In a preferred embodiment of the error pattern generation unit FME, this is embodied to apply, computer-based, automatic pattern recognition methods. (As explained above), Markov processes can be applied to the read-in data or to the input variables and used to generate the error patterns fmu.

The pattern recognition methods or the machine-learning methods are preferably executed on a processor P. In addition, the processor P can execute further algorithms, such as, for example, data mining methods and/or statistical data processing methods.

In a preferred embodiment of the invention, specific rules are provided to generate the error patterns fmu. This is intended to ensure that the error patterns fmu to be generated are adapted as well as possible to the current technical conditions of the medical devices and hence that the quality of the result with the exchange data record ad is a high as possible. To this end, it is provided that the error pattern generation unit FME interacts with a rule base RDB in which rules for generating the error patterns fmu are stored. The rules can also be dynamically changed or adapted during operation, i.e. also during the use of the devices in the field (device operation phase). This enables the generation of the error patterns fmu to be adjusted in a very up-to-date and dynamic manner to the respective technical situation (for example, if the device is used in a new environment or is to be operated with a new operating system patch).

Figure 3:
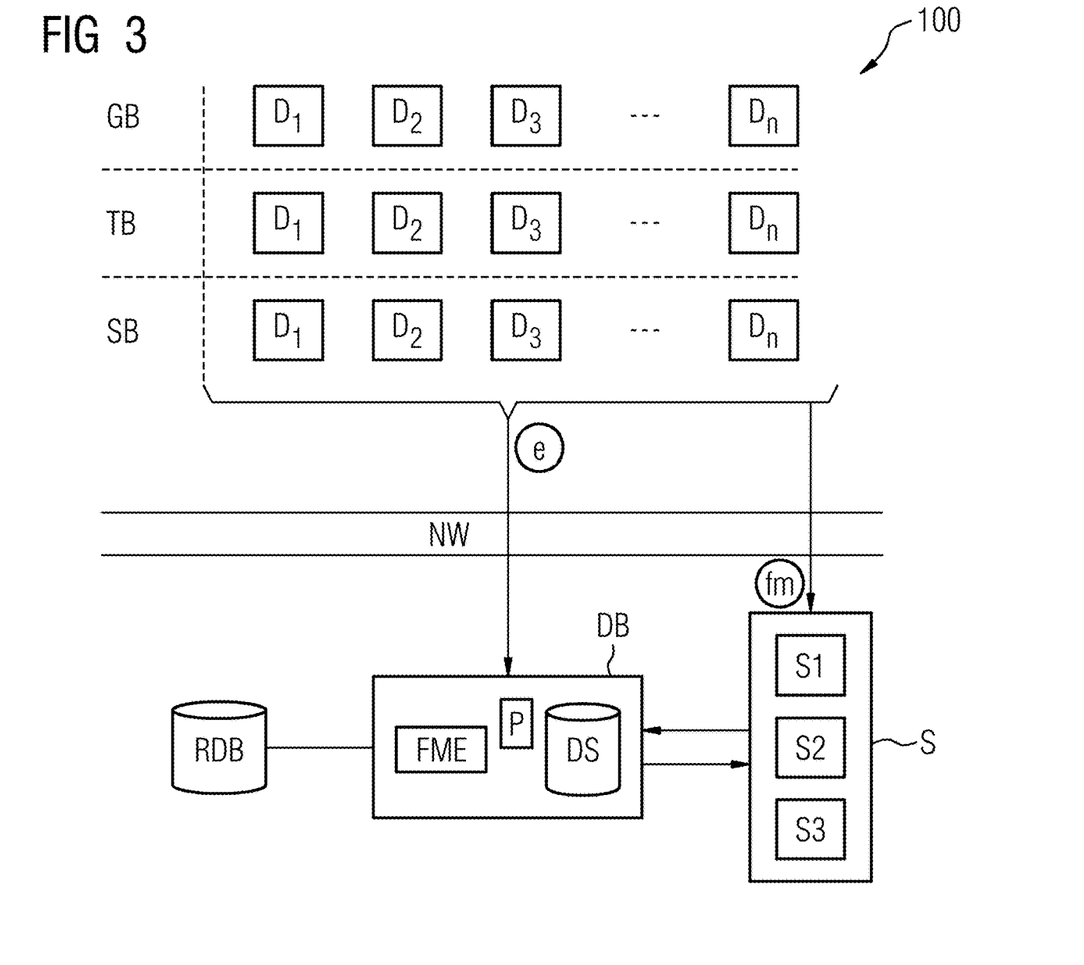
FIG. 3 is a schematic overview of the system with an error pattern generation unit in an exemplary embodiment.

The lower region of FIG. 3 depicts the calculation processor S with its further components and the database system DB with the rule base RDB. In the example depicted here, the rule base RDB is depicted as a separate database, which is connected via a corresponding interface to the database system DB. However, this embodiment is not mandatory. It can also be the case that the rule base RDB is integrated in the database system DB. In this exemplary embodiment, it is further provided that the database system DB comprises a data memory DS, the processor P and the error pattern generation unit FME as separate electronic instances. Once, again this is not a mandatory requirement. In alternative embodiments, the aforementioned structural parts FME, P, DS can also be integrated in a single module of the database system DB. Alternatively, the above components can also be distributed between separate independent components so that, for example, the error pattern generation unit FME is embodied on a separate computing unit that is in data exchange with the database system DB via a data connection. The same applies to the processor P.

As schematically depicted in FIG. 3, the system 100 according to the invention comprises the medical devices D, which are in data exchange with the database system DB and the calculation processor S via the network NW.

As explained above, the method for the identification of structural parts B to be exchanged or replaced is based on automatically generated error patterns fmu stored in the database system DB. In principle, therefore, a differentiation should be made between two time phases:

1. An application phase. In this phase, the method for the identification of structural parts B to be exchanged is carried out. This phase usually corresponds to an operating phase of the respective medical device D. As soon as the medical device D, for example in clinical operation, detects an error, an error message fm is generated and forwarded via the interface to the calculation processor S so that this is able to calculate the structural part B to be replaced in order to correct the error as quickly and efficiently as possible. To this end, the calculation processor S re-accesses the error patterns and the simulation model held in the database system.
2. An error pattern generation phase. This phase enables the generation of error patterns that are to be stored in the database system DB. This phase is so-to-speak the prerequisite for performance of the structural part identification method (in the application phase according to Point 1) because the calculation processor S has to access the error patterns fmu. Therefore, this phase takes place in advance of the application phase. This phase can coincide with a simulation phase for creating the simulation model. However, the error pattern generation phase can also coincide with a test phase for the medical device D.

Since the method for the identification of structural parts B to be exchanged is embodied as a self-learning system, further data can also be collected and aggregated during the application phase as input variables for the error pattern generation unit FME.

The different time phases are to be summarized schematically in FIG. 3. In a preferred embodiment, a differentiation is made between three phases:

1. a device operation phase GB,
2. a test operation phase TB and
3. a simulation phase or a simulation operation SB.

The device operation phase relates to normal device operation in the field after delivery or product release of the medical device D. Usually, in this device operation phase, the method for the identification of structural parts B to be exchanged is applied. This corresponds to the application phase (see above). Here, error messages fm can be acquired on the devices D and forwarded to the calculation processor S, as is intended to be represented in the right-hand side of FIG. 3 by the downward-pointing arrow identified by the reference character fm for an error message.

The test operation phase TB enables a test operation of the medical device D, in particular prior to product release or delivery of the device D. Hence, the test operation phase TB takes place while still in a development period. In test operation TB, case constellations are carried out in a dedicated manner on the respective device D in order so-to-speak "deliberately" to evoke errors. These errors then result in the output of error messages fm. In this phase, error patterns fmu can be generated on a sort of test basis and exchange data ad is generated accordingly and then subjected to evaluation. The evaluation data is held in the form of evaluation data records bd in a memory of the database system DB. In this phase, the generated error patterns fmu can be subject to review or validation. This validation or evaluation is performed automatically or manually. Automatic validation can be performed using predefinable rules that assess predefined parameters, for example the duration of an outage time or the time between the error message and error rectification for the structural part replaced in each case. Hence, a rule can optimize the error correction measure (via the evaluation data record) according to the duration of the outage time. Hence, the evaluation data record bd represents a better measure of quality if the error could be corrected more quickly by the respective structural part exchange. Another rule can represent the extent of error correction. In this case, the evaluation data record bd then represents a better quality measure if the error could be corrected more comprehensively (and for example not only partially) by the respective structural part exchange. Preferably, the only error patterns fmu stored in the database system DB are those with a prespecified sufficient measure of quality. Herein, the measure of quality can be selected by the user in an upstream definition.

The simulation operation SB of the medical devices D is not real operation of the devices, but only enables the construction and use of the simulation model for the generation of an expanded database, which is used in turn to generate the error patterns fmu. The simulation operation can coincide in terms of time with the test operation phase. The simulation operation achieves the technical advantage that the structural part identification can also be performed if no operating data with real data on structural part replacements is available yet. The simulation operation enables prediction and the learning of new patterns based on test data collected in the development phase.

As depicted schematically in FIG. 3, in all three phases device operation phase GB, test operation phase TB and simulation operation SB, input variables of the medical devices D are acquired and forwarded via the network NW to the database system DB and in particular to the error pattern generation unit FME for data processing. This implementation, which is based on a self-learning system, has the technical advantage that it is also even possible for an adequate database with error patterns fmu to be provided when the respective medical device D is put into operation for the first time and hence no device operating data is yet available. Hence, the method for the identification of structural parts to be exchanged can also be carried out without operating data immediately after the first commissioning of the medical device since it is possible to use error patterns fmu which can be used in a test operation phase TB and by a simulation model.

In FIG. 3, the input variables are identified with the reference character e. These are acquired in the different phases GB, TB, SB by the respective medical devices D via the network NW and in particular forwarded to the error pattern generation unit FME. The input variables e enable the generation of the error patterns fmu. In FIG. 3, it is also identified that, in an error scenario, the medical devices in the application phase, i.e. during the real device operation in the field, generate error messages fm, which are also forwarded via the same or another network to the calculation processor S so that this generates an exchange data record ad while accessing to the database system DB and so the local unit (modality) knows which structural part B should be exchanged (replaced) so that the reported error can be rectified.

Figure 4:
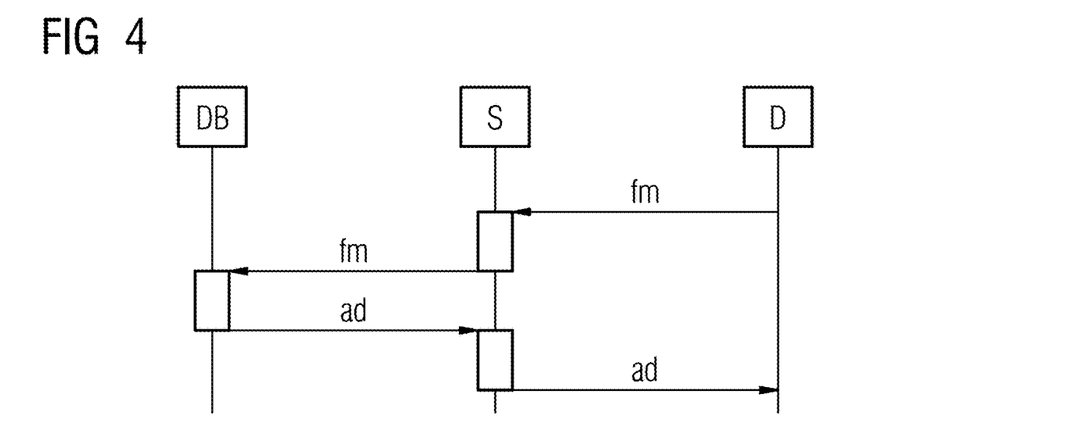
FIG. 4 is a sequence diagram depicting the data exchange between the database system, calculation processor and medical device.

FIG. 4 depicts a sequence diagram to represent the interactions involved between the database system DB, the calculation processor S and the respective medical device D. The exchanged messages depicted in FIG. 4 relate to an application phase, i.e. to a phase, in which the respective medical device D is in real operation. In an error scenario, the device D generates an error message fm which is sent from the device D to the calculation processor S. The calculation processor S reads in this error message fm and accesses the database system DB with this error message fm in order to analyze the error patterns fmu stored there in order to calculate the exchange data record ad associated with the respective error message fm. The exchange data record ad calculated by means of pattern identification analysis is then forwarded from the database system DB to the calculation processor S where it be output directly on a user interface and/or returned to the respective local medical device D in order to initiate there the appropriate error correction measures by the identification of the structural part to be exchanged. The pattern identification analysis is implemented in the identification algorithm and based on the simulation model. The above method described in connection with FIG. 4 requires error patterns fmu to have already been generated by the error pattern generation processor FME. Error-pattern generation is explained in more detail in connection with FIG. 5.

Figure 5:
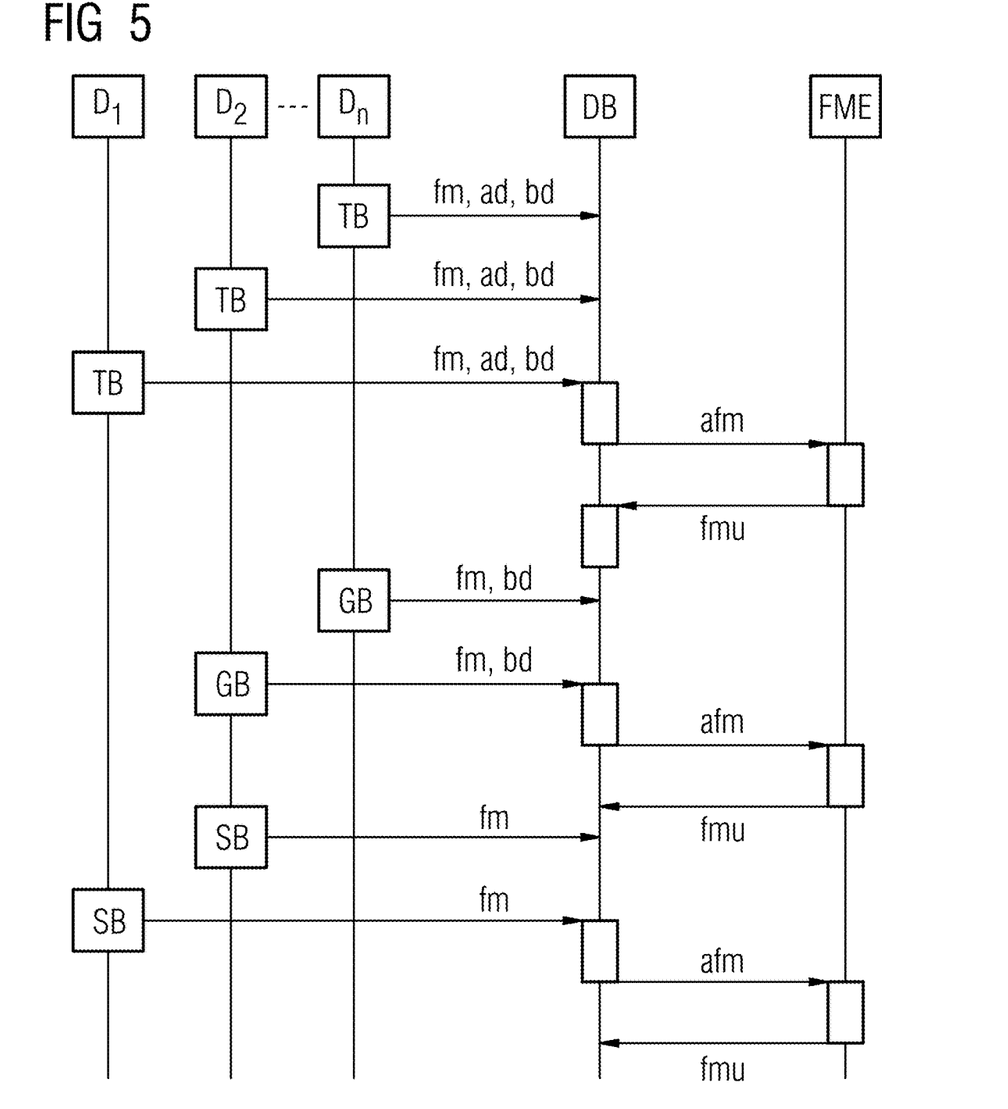
FIG. 5 is a sequence diagram depicting the data exchange between the medical devices, the database system and the error pattern generation unit.

FIG. 5 shows the message exchange between the individual medical devices D, the database system DB and the error pattern generation unit FME in order to generate the error patterns.

Input variables are acquired on the medical devices $D_1$, $D_2 \ldots D_n$ in different time phases. For the purpose of error-pattern generation and the generation of a database, the devices D can be operated both in test operation TB with test data and with simulation data. In addition, in the real field (device operation GB) it is also possible for real data (error patterns with exchange data and evaluations) to be entered into the database system in order to expand the database continuously. Herein, the different devices D can in each case be operated in one and the same time period (test/simulation and device operation) and hence acquire a different type of input variables.

For the initialization of the simulation model, in an error scenario, an error message can be associated with initial exchange data records ad, which are then subjected to evaluation. Depending upon the quality of the error correction measure, then, evaluation data records bd are generated in which the quality of the respective exchange data ad is represented. On an abstract level, it can be established that, with an adequate measure of quality, the association between error message, and exchange data is stored as an error pattern fmu in the database system DB. In the case of insufficient quality, the respective association between error message and exchange data records is not stored as an error pattern fmu. This enables it to be ensured that only a selection of error patterns is stored in the database system DB and that this only comprises error patterns fmu with a predefinable measure of quality.

In a device operation phase GB, once again input variables are acquired on the medical devices D and forwarded to the database system DB. In this phase, the database can be expanded with real data in that real error messages fm are acquired during the device operation GB and then forwarded from the database system DB to the error pattern generation unit FME in aggregated form as aggregated error messages afm. The error pattern generation unit FME can then generate error patterns fmu from the aggregated error messages afm and transmit these to the database system DB.

The application of machine-learning methods and a simulation operation SB, enables the provision of an adequate database for the error patterns fmu even at product release. This is even possible when the respective device D is not yet ready for operation in the real field (device operation GB). The method then accesses the available error patterns fmu which were generated in the test operation TB and/or in the simulation operation SB.

Figure 6:
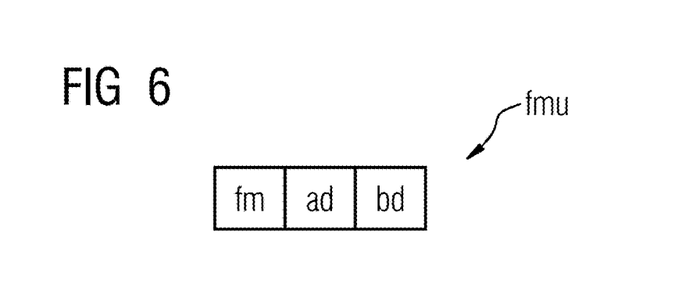
FIG. 6 is a schematic depiction of an error pattern with data fields.

FIG. 6 is a schematic depiction of an error pattern fmu. An error pattern can be stored in a tabular data structure, as depicted schematically in FIG. 6. An error pattern fmu comprises an association between in each case an error message fm, an exchange data record ad and an evaluation data record bd. Herein, an error message fm can only be associated with precisely one exchange data record ad or an error message fm can also be associated with a plurality of exchange data records ad. The latter case indicates the situation in which, in response to an error message fm, a number of structural parts B is to be exchanged to enable the error to be corrected. It is also possible for a plurality of error messages to have the same exchange data record ad. This means that the exchange of one and the same structural part B results in the error correction in the case of different error messages. As described above, the evaluation data bd represents the quality of the exchange or the generated exchange data ad.

An important advantage of the proposal according to the invention can be considered to be that the learned error patterns, which have been learned on a first set of medical devices, can also be automatically transferred to a second set of medical devices. This is technically possible because the evaluation data record bd was also added to the respective error message fm and the exchange data record ad. Processing the evaluation data record bd enables continuous improvement of the error patterns generated. Over the years of the device operation GB, the machine-learning method generates increasingly frequent and better error patterns fmu. The proposal according to the invention enables an overall increase in the quality of error correction measures since the structural parts B to be exchanged can be uniquely identified and also enables maintenance costs to be reduced, since it is now automatically possible for a proposal for the structural part exchange to be generated without requiring an on-site service engineer.

The inclusion and processing of evaluation data bd to form the generated error patterns fmu enables the error patterns to be continuously learned and improved over the course of time.

In a preferred embodiment, the identification algorithm 22 uses mathematical and stochastic optimization methods in order to improve the quality of the result. Therefore, it is provided in one advantageous embodiment that the exchange data record ad comprises an additional metadata field. The metadata can comprise information on the optimization methods, for example it can in particular indicate the measure of test coverage and the measure of correctness. This has the advantage that a client on the medical device D is able to identify directly from the generated exchange data ad how the quality of the respective exchange data record ad has been evaluated and whether in particular there is a high or low degree of test coverage and/or correctness.

If, for example, the method is to be used for MR devices, these devices have more than 500 structural parts B so that the amount of data per simulated system day of an MR device D is 30,000 error messages. If it is then assumed that 100 MR devices are taken into account in parallel for one simulation operation SB, it can be assumed that there are 300 million error messages in 100 days and hence up to 1 million structural part replacements can be simulated for each system family. As already explained above, the data and the learned data from different devices D within a system family (same device type) can also be used for other devices in the same system family. This advantageously enables the basis for the machine-learning method to be expanded.

An error pattern fmu is automatically generated as a result of aggregated input variables. An error pattern fmu comprises the calculated exchange data record ad and an evaluation data record bd for a specific error message fm, possibly with further metadata for test coverage and correctness. Therefore, a generated error pattern fmu can also be called a structural part exchange pattern. An error pattern fmu represents a group of error messages fm, exchange data records ad, which have been grouped according to predefinable rules (for example a measure of the quality of the error correction).

In an initialization phase for constructing the simulation model, the latter is stored with already performed historical structural part replacements and data records relating thereto and with test data as input variables. Hence, with all error messages and subsequent structural part replacements, data is acquired comprising in particular the following data elements:
  error message or type of error message fm
  associated exchange data record ad
  evaluation data record bd
  optional: metadata comprising data on the correctness of and test coverage.

In the case of an error message and the subsequent structural part exchange, information is acquired relating to how well the error was able to be corrected by the structural part exchange. This data is entered continuously and consecutively into the database system DB. Machine-learning methods can use this data to calculate forecasts for future, as yet unknown, data. The system can also use the simulation model as the basis for forecasting exchange data records ad for new error messages fm.

Finally, reference is made to the fact that the description of the invention and the exemplary embodiments should in principle not be understood to be restrictive with respect to a specific physical implementation of the invention. All features explained and demonstrated in connection with individual embodiments of the invention can be provided in different combinations in the subject matter according to the invention in order to implement their advantageous effects simultaneously. For those skilled in the art, it is in particular evident that the invention is applicable not only for MR devices, but also for other medical devices with which structural parts have to be exchanged in an error scenario. It is also possible for the structural parts of the system to be implemented distributed on a plurality of physical products.

The invention claimed is:

1. A method for identification of structural parts of a medical device, comprising a plurality of such structural parts, that is or are to be exchanged, said method comprising:
  in a computer, reading in an error message from a medical device comprising said plurality of structural parts;
  in said computer, executing an identification algorithm, using said error message as an input to the identification algorithm, that calculates and emits, as an output of the identification algorithm, an exchange data record that identifies a structural part of the medical device to be exchanged because of said error message, by, in the execution of said identification algorithm, accessing a database in which error patterns are stored with exchanged data records that have been calculated from a simulation model of at least said medical device, so as to calculate said exchange data record associated with the error message;
  presenting said exchange data record at a display in communication with said computer; and
  compiling said error patterns associated with said exchange data records in said database by executing a machine-learning procedure based on said simulation model for continuous learning and storage of said error patterns, by correlating input variables, wherein each error pattern comprises an association between an error type, or a combination of error types, and an exchange data record designating a structural part of said medical device that is to be exchanged.

2. A method as claimed in claim 1 comprising triggering execution of said identification algorithm in said computer by said reading-in of said error message.

3. A method as claimed in claim 1 comprising implementing said identification algorithm, immediately after commissioning of said medical device, with no operating data available from said medical device.

4. A method as claimed in claim 1 comprising executing said identification algorithm, as a self-learning algorithm, wherein an evaluation data record for said self-learning algorithm is stored in the database associated with said error patterns.

5. A database system for identification of structural parts of a medical device, comprising a plurality of such structural parts, that is or are to be exchanged, said database system comprising:
  a computer configured to read in an error message from a medical device comprising said plurality of structural parts;
  a database in which error patterns are stored with exchanged data records that have been calculated from a simulation model of at least said medical device;
  said computer being configured to execute an identification algorithm, using said error message as an input to the identification algorithm, that calculates and emits, as an output of the identification algorithm, an exchange data record that identifies a structural part of the medical device to be exchanged because of said error message, by, in the execution of said identification algorithm, accessing said database so as to calculate said exchange data record associated with the error message;
  a display in communication with said computer at which said computer is configured to display said exchange data record;
  an error pattern generation processor configured to compile said error patterns associated with said exchange data records in said database by executing a machine-learning procedure based on said simulation model for continuous learning and storage of said error patterns, by correlating input variables, wherein each error pattern comprises an association between an error type, or a combination of error types, and an exchange data record designating a structural part of said medical device that is to be exchanged.

6. A database system as claimed in claim 5 wherein said error pattern generation processor is configured to generate said error patterns by reading in test data of a test operation aggregated as said input variables, with error scenarios of said medical device and associated exchange data records, in order to thereby generate said simulation model with simulation data that is continuously updated with further data.

7. A database system as claimed in claim 5 wherein said error pattern generation processor is configured to continuously expand said simulation model with additional data during operation of said medical device so as to read in, aggregated as input variables, said simulation data of a simulation operation of the medical device with error scenarios.

8. A database system as claimed in claim 5 wherein said error pattern generation processor is configured to generate said error patterns centrally from a plurality of different medical devices.

9. A database system as claimed in claim 5 wherein said error pattern recognition processor is configured to interact with a rule base, in which rules for generating said error patterns are stored.

10. A database system as claimed in claim 5 wherein said error pattern generation processor is configured to generate said error patterns dependent on an evaluation data record, representing a measure of a quality of error correction, that was acquired and stored during historical structural part replacements represented in said error message.

11. A computer for identification of structural parts of a medical device, comprising a plurality of such structural parts, that is or are to be exchanged, said computer comprising:
   an input configured to read in an error message from a medical device comprising said plurality of structural parts;
   a processor configured to execute an identification algorithm, using said error message as an input to the identification algorithm, that calculates and emits, as an output of the identification algorithm, an exchange data record that identifies a structural part of the medical device to be exchanged because of said error message, by, in the execution of said identification algorithm, accessing a database in which error patterns are stored with exchanged data records that have been calculated from a simulation model of at least said medical device, so as to calculate said exchange data record associated with the error message;
   a display in communication with said processor at which said processor is configured to display said exchange data record; and
   an error pattern generation processor configured to compile said error patterns associated with said exchange data records in said database by executing a machine-learning procedure based on said simulation model for continuous learning and storage of said error patterns, by correlating input variables, wherein each error pattern comprises an association between an error type, or a combination of error types, and an exchange data record designating a structural part of said medical device that is to be exchanged.

12. A medical system comprising:
   a medical device comprising a plurality of such structural parts, that is or are to be exchanged;
   a computer configured to read in an error message from said medical device comprising said plurality of structural parts;
   said computer being configured to execute an identification algorithm, using said error message as an input to the identification algorithm, that calculates and emits, as an output of the identification algorithm, an exchange data record that identifies a structural part of the medical device to be exchanged because of said error message, by, in the execution of said identification algorithm, accessing a database in which error patterns are stored with exchanged data records that have been calculated from a simulation model of at least said medical device, so as to calculate said exchange data record associated with the error message;
   a display in communication with said computer at which said computer is configured to display said exchange data record; and
   an error pattern generation processor configured to compile said error patterns associated with said exchange data records in said database by executing a machine-learning procedure based on said simulation model for continuous learning and storage of said error patterns, by correlating input variables, wherein each error pattern comprises an association between an error type, or a combination of error types, and an exchange data record designating a structural part of said medical device that is to be exchanged.

13. A non-transitory, computer-readable data storage medium encoded with programming instructions, said storage medium being loaded into a computer associated with a medical system comprising at least one medical device, said programming instructions causing said computer to:
   read in an error message from a medical device comprising said plurality of structural parts;
   execute an identification algorithm, using said error message as an input to the identification algorithm, that calculates and emits, as an output of the identification algorithm, an exchange data record that identifies a structural part of the medical device to be exchanged because of said error message, by, in the execution of said identification algorithm, accessing a database in which error patterns are stored with exchanged data records that have been calculated from a simulation model of at least said medical device, so as to calculate said exchange data record associated with the error message;
   present said exchange data record at a display in communication with said computer; and
   compile said error patterns associated with said exchange data records in said database by executing a machine-learning procedure based on said simulation model for continuous learning and storage of said error patterns, by correlating input variables, wherein each error pattern comprises an association between an error type, or a combination of error types, and an exchange data record designating a structural part of said medical device that is to be exchanged.

14. A method as claimed in claim 1 comprising generating said error patterns by reading in test data of a test operation aggregated as said input variables, with error scenarios of said medical device and associated exchange data records, in order to thereby generate said simulation model with simulation data that is continuously updated with further data.

15. A method as claimed in claim 1 comprising continuously expanding said simulation model with additional data during operation of said medical device so as to read in, aggregated as input variables, said simulation data of a simulation operation of the medical device with error scenarios.

16. A method as claimed in claim 1 comprising generating said error patterns dependent on an evaluation data record, representing a measure of a quality of error correction, that was acquired and stored during historical structural part replacements represented in said error message.

17. A computer as claimed in claim 11 wherein said error pattern generation processor is configured to generate said error patterns by reading in test data of a test operation aggregated as said input variables, with error scenarios of said medical device and associated exchange data records, in order to thereby generate said simulation model with simulation data that is continuously updated with further data.

18. A database system as claimed in claim 11 wherein said error pattern generation processor is configured to continuously expand said simulation model with additional data during operation of said medical device so as to read in, aggregated as input variables, said simulation data of a simulation operation of the medical device with error scenarios.

19. A database system as claimed in claim 11 wherein said error pattern generation processor is configured to generate said error patterns dependent on an evaluation data record, representing a measure of a quality of error correction, that was acquired and stored during historical structural part replacements represented in said error message.

20. A medical system as claimed in claim 12 wherein said error pattern generation processor is configured to generate said error patterns by reading in test data of a test operation aggregated as said input variables, with error scenarios of said medical device and associated exchange data records, in order to thereby generate said simulation model with simulation data that is continuously updated with further data.

21. A medical system as claimed in claim 12 wherein said error pattern generation processor is configured to continuously expand said simulation model with additional data during operation of said medical device so as to read in, aggregated as input variables, said simulation data of a simulation operation of the medical device with error scenarios.

22. A medical system as claimed in claim 12 wherein said error pattern generation processor is configured to generate said error patterns dependent on an evaluation data record, representing a measure of a quality of error correction, that was acquired and stored during historical structural part replacements represented in said error message.

23. A non-transitory, computer-readable data storage medium of claim 13 further encoded with programming instructions causing said computer to:
generate said error patterns by reading in test data of a test operation aggregated as said input variables, with error scenarios of said medical device and associated exchange data records, in order to thereby generate said simulation model with simulation data that is continuously updated with further data.

24. A non-transitory, computer-readable data storage medium of claim 13 further encoded with programming instructions causing said computer to:
continuously expand said simulation model with additional data during operation of said medical device so as to read in, aggregated as input variables, said simulation data of a simulation operation of the medical device with error scenarios.

25. A non-transitory, computer-readable data storage medium of claim 13 further encoded with programming instructions causing said computer to:
generate said error patterns dependent on an evaluation data record, representing a measure of a quality of error correction, that was acquired and stored during historical structural part replacements represented in said error message.

* * * * *